US011395723B2

(12) United States Patent
Jalali et al.

(10) Patent No.: US 11,395,723 B2
(45) Date of Patent: Jul. 26, 2022

(54) SURGICAL DEVICE AND METHODS OF USE

(71) Applicants: The Texas A&M University System, College Station, TX (US); Webb Medical, LLC, Philadelphia, PA (US)

(72) Inventors: Sid Poorya Jalali, Dallas, TX (US); David Krupnick, Philadelphia, PA (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/134,506

(22) Filed: Sep. 18, 2018

(65) Prior Publication Data

US 2020/0085553 A1 Mar. 19, 2020

(51) Int. Cl.
| | |
|---|---|
| *A61C 19/04* | (2006.01) |
| *A61B 6/00* | (2006.01) |
| *A61B 90/00* | (2016.01) |
| *A61C 5/40* | (2017.01) |
| *A61B 6/14* | (2006.01) |
| *A61B 6/03* | (2006.01) |

(52) U.S. Cl.
CPC ............ *A61C 19/042* (2013.01); *A61B 6/032* (2013.01); *A61B 6/145* (2013.01); *A61B 6/4085* (2013.01); *A61B 90/39* (2016.02); *A61C 5/40* (2017.02); *A61B 2090/3966* (2016.02)

(58) Field of Classification Search
CPC ......... A61C 19/042; A61C 5/40; A61C 19/04; A61C 5/44; A61B 90/39; A61B 6/032; A61B 6/4085; A61B 6/145; A61B 2090/3966; A61B 6/03; A61B 6/02; A61B 34/20; A61B 2090/3983; A61B 2090/373; A61B 2090/3937; A61B 2034/2057; A61B 2034/2055; A61B 2034/2065; G06T 7/74; G06T 7/593; G06T 2207/10012; G06T 2207/30036; G06T 2207/30204
USPC ........................................................ 433/29
See application file for complete search history.

(56) References Cited

U.S. PATENT DOCUMENTS

| | | | | | |
|---|---|---|---|---|---|
| 2,711,021 | A | * | 6/1955 | George ................. | A61C 13/30 433/175 |
| 3,770,956 | A | * | 11/1973 | Johnson ............... | G03B 42/047 378/164 |
| 4,394,770 | A | * | 7/1983 | La Franca ............. | G03C 3/003 378/164 |
| 4,866,750 | A | * | 9/1989 | Chavarria ............ | G03B 42/042 378/168 |

(Continued)

*Primary Examiner* — Nicholas D Lucchesi
*Assistant Examiner* — Mirayda A Aponte
(74) *Attorney, Agent, or Firm* — Husch Blackwell LLP (57) ABSTRACT

A surgical device for identification of a surgical site of interest, such as a craniofacial or dental site (root apex of an identified tooth), and a method for using the device is provided. The device includes a perimeter bar and a plurality of intermediate cross bars arranged in a grid structure. The device can be used during a surgical procedure requiring enhanced precision, such as during an endodontic surgical procedure, by positioning the device next to a patient's tooth and capturing a CBCT image, the CBCT image being used to identify a drilling location. The device can be repositioned alongside the patient's tooth, and used to identify an accurate drilling position.

18 Claims, 8 Drawing Sheets

(56) References Cited

U.S. PATENT DOCUMENTS 5,285,785 A * 2/1994 Meyer .................... A61B 6/12
33/512
7,508,919 B2 * 3/2009 Young .................... A61C 1/084
378/164

* cited by examiner

SURGICAL DEVICE AND METHODS OF USE

BACKGROUND OF THE INVENTION

Dental professionals often use endodontic surgery (apicoectomy) as a surgical treatment option for a damaged, injured, or infected tooth, particularly when root canal treatment is unsuccessful. In this procedure, the gum tissue near the tooth is opened to see the underlying bone and to remove any inflamed or infected tissue. The very end of the root is also removed. One of the challenges of this procedure is identifying the exact location of the tip (or apex) of the root. In order to locate the root apex, an osteotomy is often performed on the affected tooth to remove the bone covering the apex of the root and to make a small window to the apex. Many times, in an attempt to find the apex of the root, the dental professional may remove an unnecessary amount of bone during the osteotomy procedure. Not only is this an undesirable result for the tooth, it also may risk damage to the vital structures near the root (e.g., nerve, sinus). According to the American Association of Endodontists, approximately 15 million root canal treatments are performed every year in the United States, and approximately 10-15 percent of root-canal treated teeth fail and require further surgical or non-surgical treatment. As a result, thousands of endodontic surgical procedures are performed every year in the United States The most common method used to detect the location of the root apex is to use Cone Beam Computed Tomography (CBCT). CBCT is a CT scan with a very small field of view and is commonly used in dentistry. CBCT scans have less radiation, but a higher resolution compared to a medical CT scan. However, while the CBCT scan allows the dental professional to identify the location of the root apex, it is difficult for dental professionals to use the CBCT scan results to accurately locate the root apex during actual surgery. This is, at least in part, because it is difficult to transfer the information gained from the CBCT scan (which has a very small field of view) to a real patient during surgery.

One industry solution to the problem described above is image guided surgery. In an endodontic surgical procedure utilizing image guided surgery, a digital impression device is used to create a digital impression of the patient's teeth, and the digital impression is combined with a CBCT scan to provide a guide that is created with a 3-D printer. However, this solution is not efficient or effective because it requires the use of both a digital impression device and a 3-D printer, which are not common among endodontists and other dental professionals, are expensive, and are time consuming to use.

Accordingly, a need continues to exist for a device and method for accurately locating the root apex of a tooth.

SUMMARY OF THE INVENTION

The present invention relates generally to a device configured for assisting professionals, and particularly craniofacial and dental surgical professionals and endodontists, in accurately identifying the location of a desired surgical site by Cone Beam Computed Tomography (CBCT). CBCT is a CT scan with a very small field of view. CBCT may therefore be used according to the present invention together with the described techniques and tools by the dental or other surgical professional to precisely map the root tip (or apex) of a patient's tooth, and this information may then be transferred to the herein described device. The device may thus be utilized in this manner to precisely remove the located structure, such as a root tip (apex) or other structure. The device can be used to easily and accurately map the desired structure, such as the root apex location information identified on a CBCT scan image, and transfer that information to the surgical device during the surgical procedure.

In some embodiments, the device can comprise a perimeter rim defining an opening therein and a plurality of intermediate cross bars arranged in a grid pattern or grid structure spanning across the opening. The device can be configured for use in connection with a CBCT scan to identify a position on the device that corresponds to a location of a surgical location of interest, such as tooth drilling location for exposing the root apex of an identified tooth in a patient to be operated on. For example, during an endodontic surgical procedure, the dental professional can use the device as a guide by locating the previously identified position on the device that corresponds to the drilling location and using the device as a guide for drilling the patient's tooth to expose the root apex of the tooth. The root apex can then be removed and the endodontic surgical procedure can be completed.

According to one embodiment, the device can include a plurality cross bars. According to one embodiment, the device can include a plurality of cross bars extending in a singular direction. According to one embodiment, the device can include a plurality of longitudinal or horizontal cross bars and a plurality of latitudinal or vertical cross bars. According to one embodiment, the longitudinal cross bars are uniformly spaced and parallel to one another, and the latitudinal cross bars are uniformly spaced and parallel to one another.

The device may take on several configurations. For example, the device may have a rectangular, square, oval, or other configuration.

According to one embodiment the device is constructed from a radiopaque material.

According to one embodiment, the device includes a locator dot connected to the cross bars to be used as an identifier. According to one embodiment, the locator dot is centrally located within the opening of the device and secured to the intermediate cross bars.

In some embodiments, a method for using the device as a dental surgical assistance device is provided. For example, the device is used while performing endodontic surgery in order to assist a dental professional in accurately identifying the precise location of the root apex for the tooth to be operated on during the surgical procedure. According to one embodiment, the method can comprise the steps of: providing a grid-pattern guide device adjacent to an identified tooth and capturing a cone beam computed tomography scan image of the grid-pattern guide device and the identified tooth, wherein the grid-pattern guide device comprises a grid structure having a plurality of intermediate cross bars; identifying a guide position on the grid-pattern guide device by determining a pre-planned drilling location on the cone beam computed tomography scan image corresponding to a position on the identified tooth where the root apex is located and selecting a location on the grid-pattern guide device that corresponds to the pre-planned drilling location; and using the grid-pattern guide device during the endodontic surgical procedure by locating the guide position on the grid-pattern guide device and drilling the individual tooth at a drill location associated with the guide position to expose the root apex of the patient's tooth.

Other aspects and advantages of the present invention will be apparent from the following detailed description of the preferred embodiments of the accompanying drawing figures.

DESCRIPTION OF THE SEVERAL VIEWS OF THE DRAWING

In the accompanying drawing, which forms a part of the specification and is to be read in conjunction therewith in which like reference numerals are used to indicate like or similar parts in the various views.

DETAILED DESCRIPTION OF THE INVENTION

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

Turning to the several figures, the present invention is directed to a dental surgical assistance device 10 and a method 100 for using the same. Device 10 can be used during dental surgical procedures, particularly endodontic or apicoectomy surgical procedures where the root apex or tip of an identified tooth, such as an injured or damaged tooth, is removed along with surrounding damaged tissue. During such procedures, a small amount of tooth bone is removed near the root end to access and remove the root apex; however, because the tooth bone blocks access to the root apex, it is difficult to accurately identify the location of the root apex during the actual surgical procedure. As described herein, device 10 can be used as a guide to assist a dental professional in accurately identifying the precise location of the root apex during the actual surgical procedure by using device 10 in connection with a CBCT scan of the patient's tooth to identify the location of the root apex relative to device 10 and then using device 10 as a guide during the actual surgical procedure.

Figure 1:
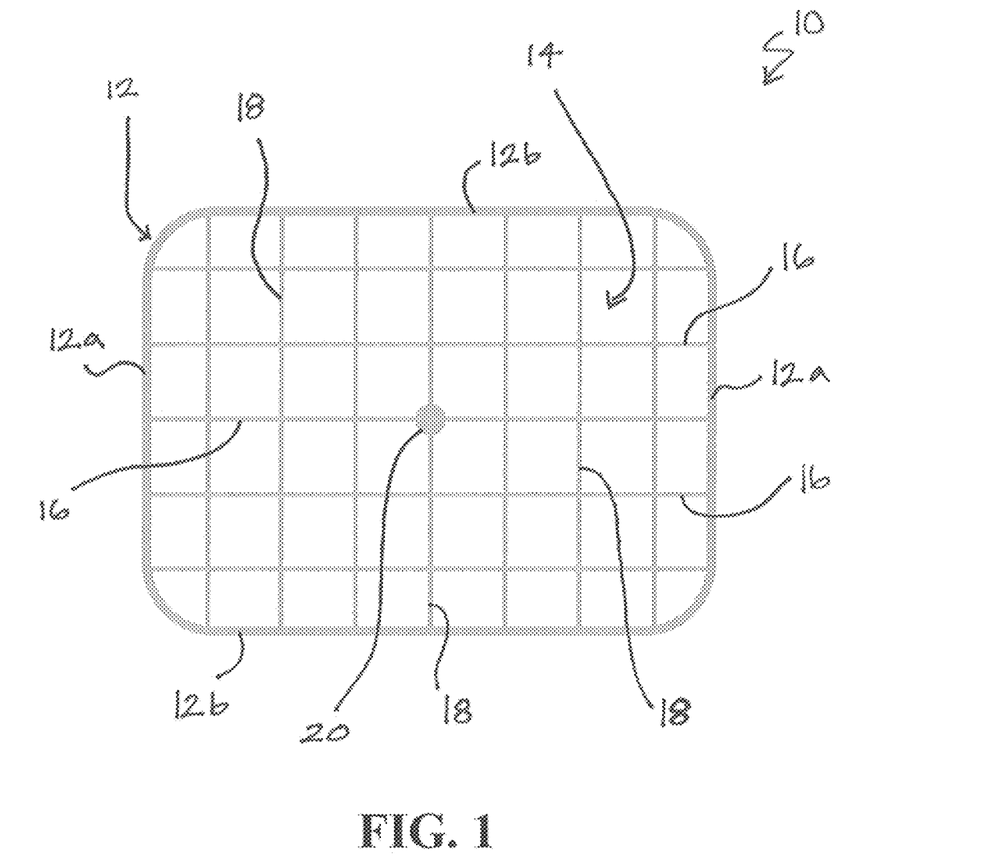
FIG. 1 is a plan view of a dental surgical assistance device in accordance with one embodiment of the present invention.
Figure 2:
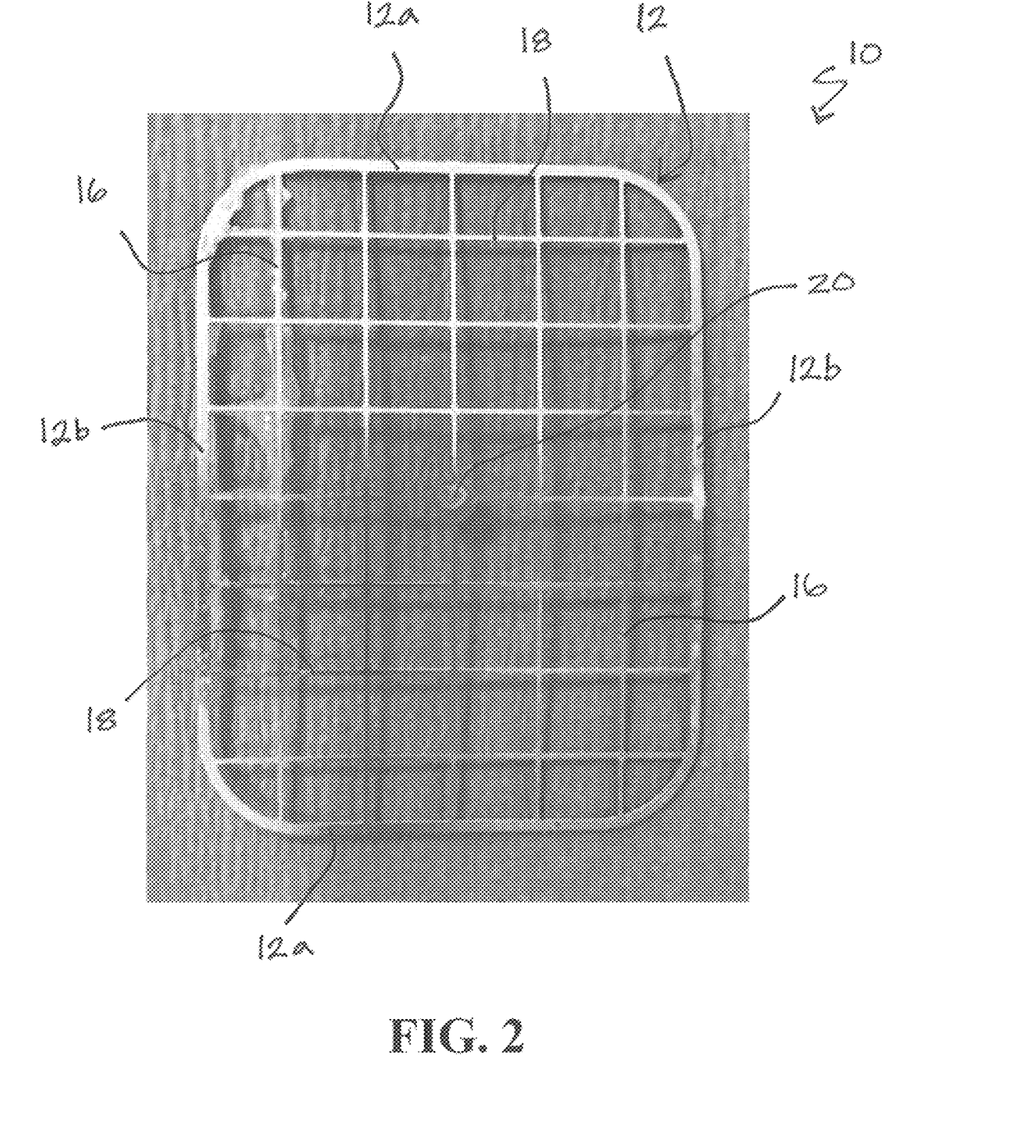
FIG. 2 is a photographic plan view of a dental surgical assistance device in accordance with one embodiment of the present invention.

FIGS. 1 and 2 show device 10 in accordance to one embodiment of the present invention. As shown in FIGS. 1 and 2, device 10 can include an enclosed exterior perimeter rim 12 that defines an opening or window 14 therein. Exterior perimeter rim 12 can be configured as a continuous or connected bar that extends around all or part of device 10. As further shown in FIG. 1, provided within opening 14 can be a plurality of intermediate, spaced cross bars 16 and 18 that extend between the top, bottom and side edges of perimeter rim 12 and are arranged in a grid pattern to provide device 10 with a grid-type structure. Cross bars 16 can be configured as intermediate longitudinal cross bars 16 that extend generally horizontally between the side edges 12a of perimeter rim 12 and across opening 14. Cross bars 18 can be configured as intermediate latitudinal cross bars 18 that extend generally vertically between the top and bottom edges 12b of perimeter rim 12 and across opening 14.

According to certain embodiments, device 10 can be configured with only a single set of cross bars 16, which can be orientated in the vertical, horizontal, diagonal or other desired direction. In such embodiments cross bars 16 extend in a similar direction and do not form a cross or overlapping type grid pattern, but instead a singular-type grid pattern or structure.

In addition, according to certain embodiments (not shown) device 10 can be encapsulated in a component having a punch through feature that could allow for reduced gum irritation during a surgical procedure. For example, all or part of perimeter rim 12 can have a cover or coating (such as, but not limited to a small rubber or foam sleeve) that can make device 10 more comfortable in the gum cavity of the patient.

As best shown in FIG. 1, according to one embodiment, cross bars 16 and 18 can be uniformly or equally spaced apart along edges 12a and 12b of perimeter rim 12 to provide a uniform grid pattern within opening 14. In such a configuration, cross bars 16 can extend parallel to one another and perpendicular to cross bars 18, while cross bars 18 can extend parallel to one another and perpendicular to cross bars 16. According to one embodiment of the present invention, cross bars 16 and 18 can be spaced approximately five millimeters (5 mm) apart; however, it is recognized that any other spacing dimension can be suitably used in other embodiments of the invention. Collectively, cross bars 16 and 18 can create a grid pattern within opening 14 that can enable a particular location within opening 14 to be accurately and easily located. For example, as described in greater detail below, when device 10 is used with a CBCT scan, the root apex location of an injured tooth on the CBCT scan can be identified within the grid pattern of device 10 by determining the root apex's position relative to a particular cross bar 16 and a particular cross bar 18 and the particular position on device 10 can be used to identify the root apex location during a surgical procedure.

In addition, while not necessarily illustrated in the figures, according to certain embodiments of the present invention, cross bars 16 and 18 of device 10 need not necessarily have exact spacing to operate as an identifier. For example, according to one embodiment (not shown), cross bars 16 can have singular odd spacing where specific cross bars 16 have are spaced greater than others. Similarly, in certain embodiments (not shown), cross bars 18 can have individualized, non-uniform spacing. In other embodiments, cross bars 16 can have uniform and cross bars 18 have non-uniform spacing, and in yet other embodiments, cross bars 16 can have uniform spacing that is different than the uniform spacing of cross bars 18. Such irregular, singular and/or non-uniform spacing can also function as an identifier for accurately locating root apex locations. Accordingly, cross bars 16 and 18 can have any desired orientation, spacing, shape and configuration within perimeter rim 12 depending on the particular application and use of device 10 in alternative embodiments of the present invention.

As further shown in FIGS. 1 and 2, according to one embodiment of the present invention, device 10 can have a generally rectangular shape defined by perimeter rim 12; however, in alternative embodiments, device 10 can have a circular or other desired shape.

As also shown in FIGS. 1 and 2, according to one embodiment of the present invention, device 10 can include a locator dot 20 provided within opening 14. As shown in FIGS. 1 and 2, locator dot 20 can be generally centrally located within opening 14. According to one embodiment, locator dot 20 can be positioned at the intersection of the center-most cross bars 16 and 18 and can be circular (as shown in FIG. 1), rectangular or any other desired shape (not shown). In such an embodiment, locator dot 20 is centrally located within opening 14; however, it is recognized that locator dot 20 can be positioned anywhere within opening 14 in alternative embodiments of the present invention. In addition, according to certain embodiments, locator dot 20 can be selectively removable from cross bars 16/18 in order to enable locator dot to be selectively positioned at any desired location within opening 14. Locator dot 20 can be used to assist in the identification of a specific location within the grid pattern of device 10, such as without limitation, on a CBCT scan when the entire device 10 is not captured within the narrow field of view of the CBCT scan image.

In order to allow device 10 to be utilized in connection with a CBCT scan, device 10 (including rim 12, cross bars 16 and 18, and locator dot 20) can be constructed from a radiopaque material or alloy or other suitable material that allows device 10 to provide a clear image of device 10, and it grid pattern defined by cross bars 16 and 18, within a CBCT scan image. According to one embodiment, as shown in FIG. 2, device 10 can be constructed from titanium. Alternatively, device 10 can be constructed from tungsten, stainless steel or other suitable material. In addition, device 10 can also incorporate ink mixes that can create radiopaque functionality.

Figure 3:
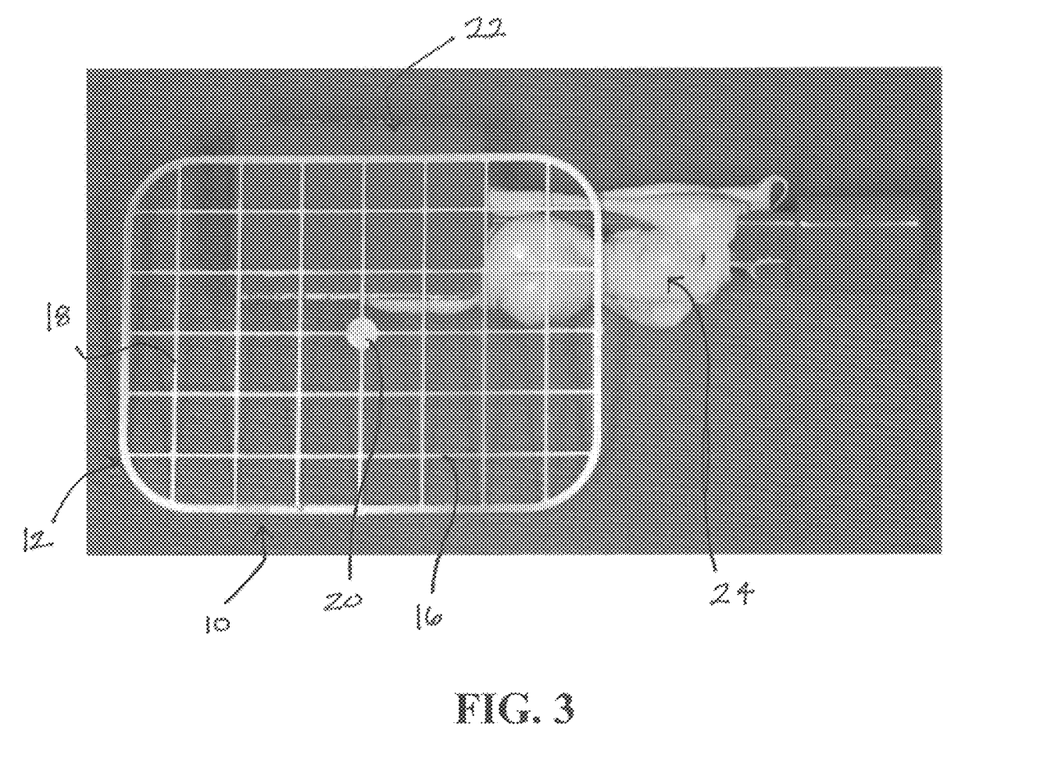
FIG. 3 is a perspective view of a dental surgical assistance device in accordance with one embodiment of the present invention illustrating the dental surgical assistance device attached to an adhesive surface of a bitewing holder having bite registration material applied thereon to enable reproducible positioning of the bitewing holder and dental surgical assistance device combination.
Figure 4:
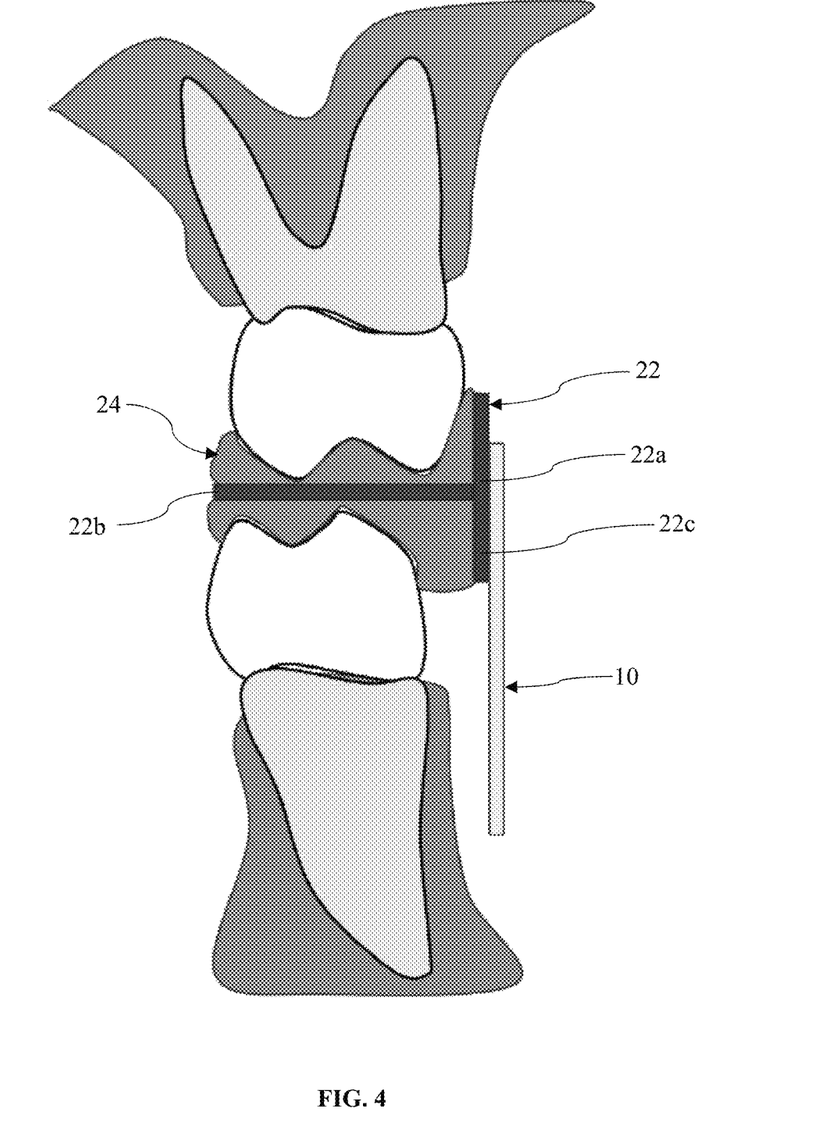
FIG. 4 is a schematic elevation view the dental surgical assistance device of FIG. 1 illustrating the dental surgical assistance device attached to a bitewing holder with bite registration material applied thereon and being used for CBCT scanning.

Turing to FIGS. 3 and 4, the device 10 can be used in connection with a bitewing film holder 22 (which can be any standard bitewing film holder) and impression material 24 (such as registration wax or fast setting impression material) to enable device 10 to serve as a guide assistance tool during an endodontic surgical procedure. The bitewing film holder 22 as shown has a film portion 22a with an exterior side 22c, and a lateral bite tab 22b. As shown in FIG. 3, device 10 can be attached to bitewing film holder 22 in a fixed position and the impression material 24 can be placed on bitewing holder film 22. Then, as shown in FIG. 4, the bitewing of a patient can be registered using the impression material 24 so that the dental professional can reproduce the precise location of device 10 when used during surgery.

As described above, device 10 can be used by a dental professional during an endodontic surgical procedure in order to allow the dental professional to accurately identify the location of the root apex of a patient's injured tooth during surgery. This can, among other things, minimize the amount of tooth bone removed during surgery to access and remove the root apex. Prior to the surgical procedure, device 10 can be secured to a bitewing holder 22 (see FIG. 3) and device 10 can be positioned on the side of the injured tooth. The patient can then be requested to bite on the bitewing holder 22 and a CBCT scan can be taken of the injured tooth. The bitewing holder 22 can have impression material 24 applied thereon (see FIG. 4) so that the precise positioning of device 10 relative to the injured tooth during the CBCT scan can be reproduced during surgery. On the CBCT scan, device 10 and its cross bars 16 and 18 will be displayed as white lines overlying the patient's injured tooth. The dental professional can then identify the location of the root apex of the injured tooth on the CBCT scan. In addition, the dental professional can further identify a guide position on device 10 that corresponds to the location of the root apex relative to the grid pattern of device 10. For example, on the CBCT scan, the dental professional can identify the root apex location to be associated with the intersection of a particular longitudinal cross bar 16 and particular latitudinal cross bar 18. Further, in the event the CBCT scan does not capture the entire grid pattern of device 10, locator dot 20 can be utilized to identify the precise location of the grid pattern of device 10 as it relates to the root apex location.

Following the identification of the root apex location and corresponding location (i.e., guide position) on the grid pattern of device 10, device 10 can be used as a guide during the actual surgical procedure. Device 10 can be repositioned on the side of the patient's injured tooth (via the bite registration made by the impression material) so that device 10 is in the same position relative to the injured tooth during the CBCT scan. The dental professional can then locate the location on the grid pattern of device 10 that was identified in the CBCT scan and use that location to know exactly where to drill into the tooth bone in order to expose and remove the root apex. As a result, device 10 can be utilized as a guide to enable the dental professional to identify the exact location to be drilled so that the root apex can be exposed and removed with minimal excess bone removal.

Figure 5A:
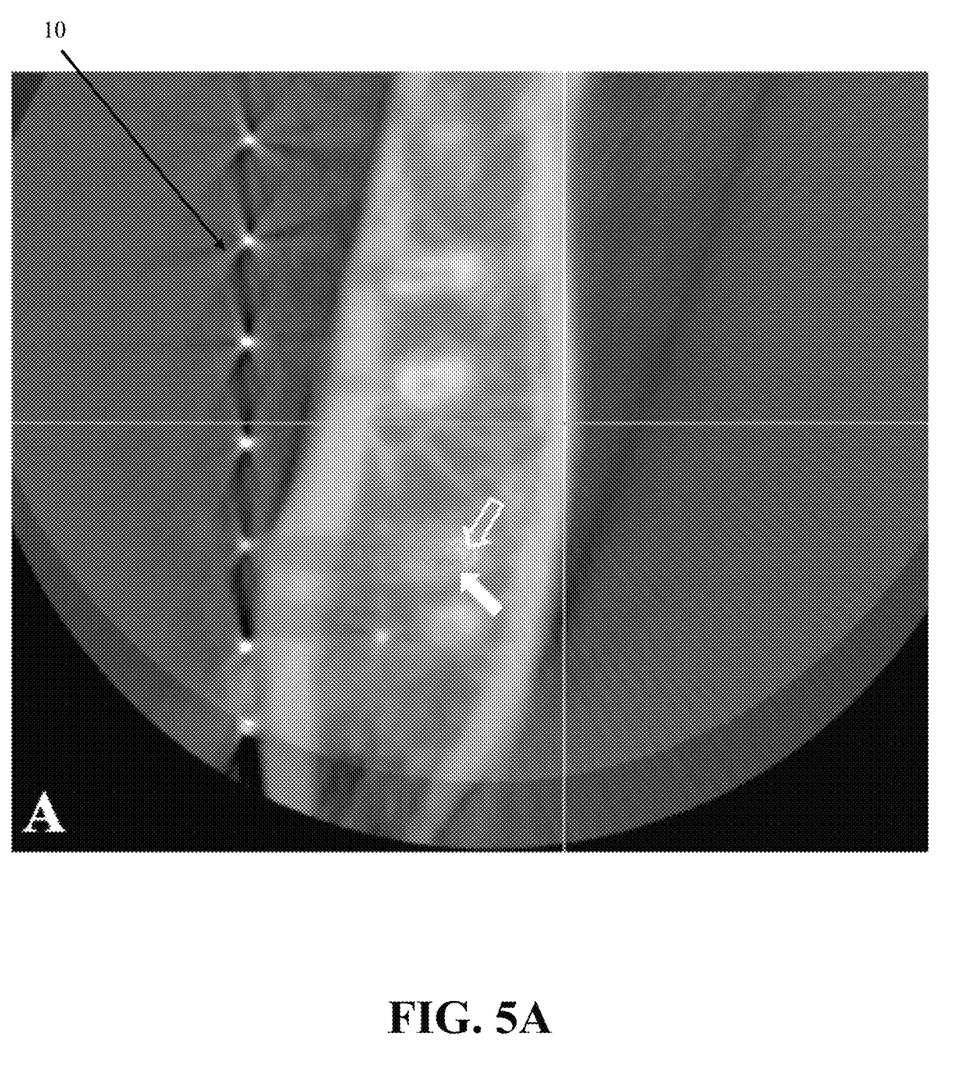
FIG. 5A is a schematic view of superimposed preoperative and postoperative CBCT scans in axial view illustrating a preplanned drill path and actual drill path performed utilizing a dental surgical assistance device in accordance with one embodiment of the present invention.
Figure 5B:
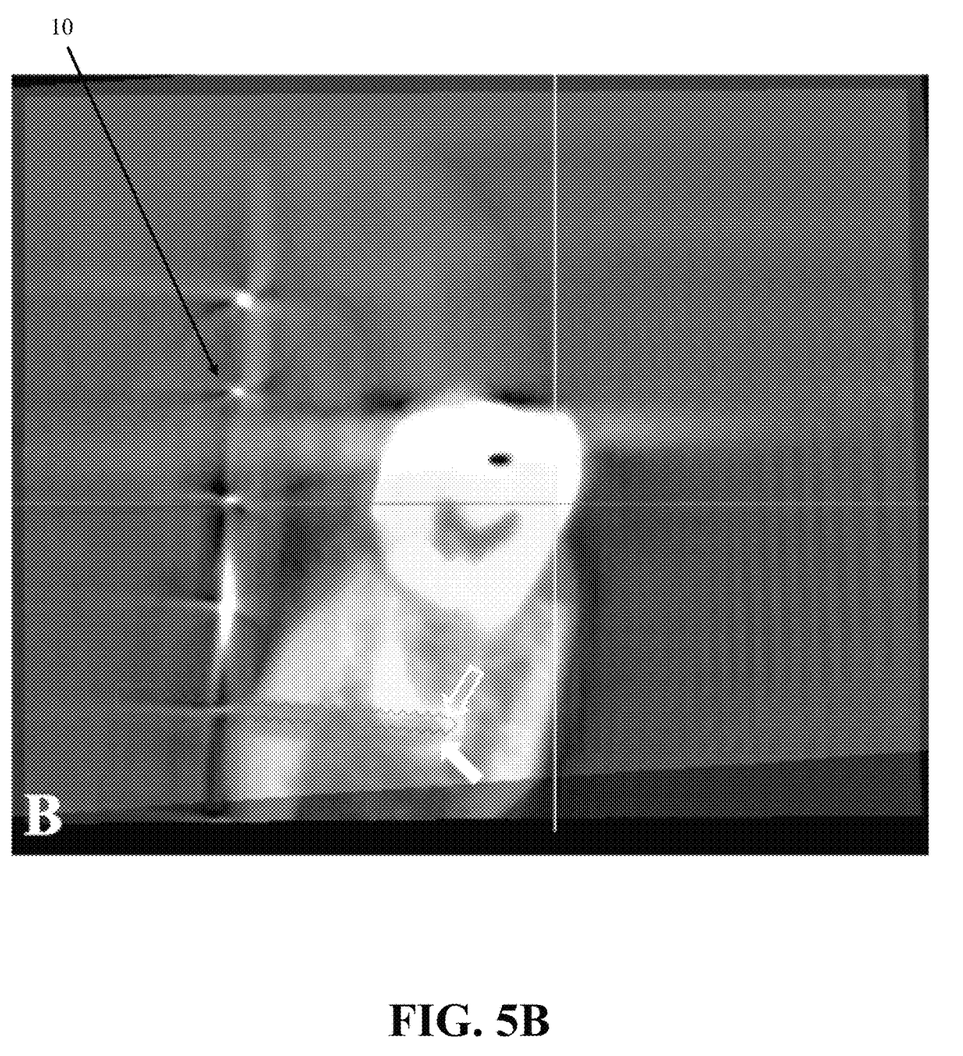
FIG. 5B is a schematic view of superimposed preoperative and postoperative CBCT scans in sagittal view illustrating a preplanned drill path and actual drill path performed utilizing a dental surgical assistance device in accordance with one embodiment of the present invention.

FIGS. 5A and 5B provide illustrative pre- and post-operative CBCT scans showing how device 10 can be effectively used to identify the root apex drilling location during an endodontic surgical procedure. As described above, the grid pattern of device 10 enables a dental professional to identify a preplanned drill path on a CBCT scan for exposing the root apex of an injured tooth. Once identified, the location of that preplanned drill path can be matched to a guide position on the grid pattern of device 10.

Subsequently, during the actual surgery, the guide position on device 10 can used as a guide to accurately follow the preplanned drill path. FIGS. 5A and 5B provide illustrative CBCT scans in axial and sagittal views, respectively, showing the location of the preplanned drill path (hollow arrow) and the actual drill path (solid arrow) of an endodontic surgical procedure performed using device 10. As illustrated in the figures, device 10 enabled the dental professional to execute the preplanned drill path with increased accuracy.

Figure 6:
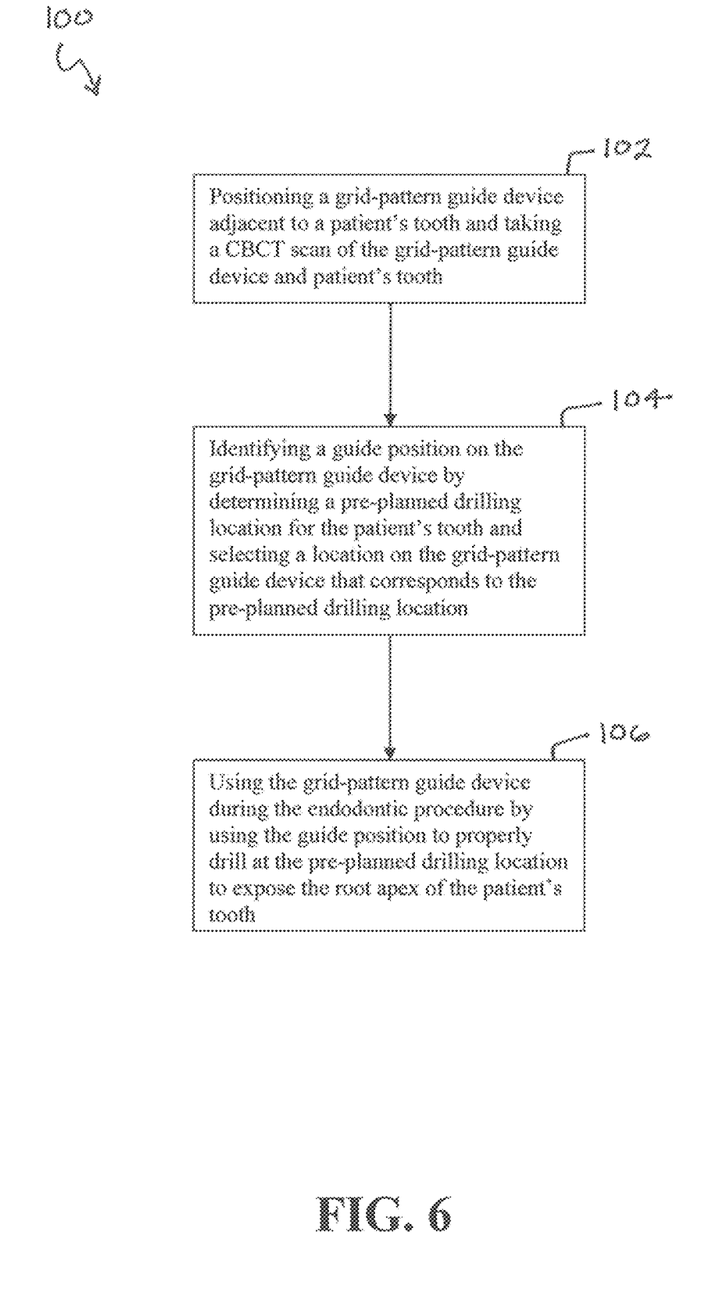
FIG. 6 is a flow chart for a method for using a grid-pattern guide device to perform an endodontic surgical procedure in accordance with one embodiment of the present invention.
Figure 7:
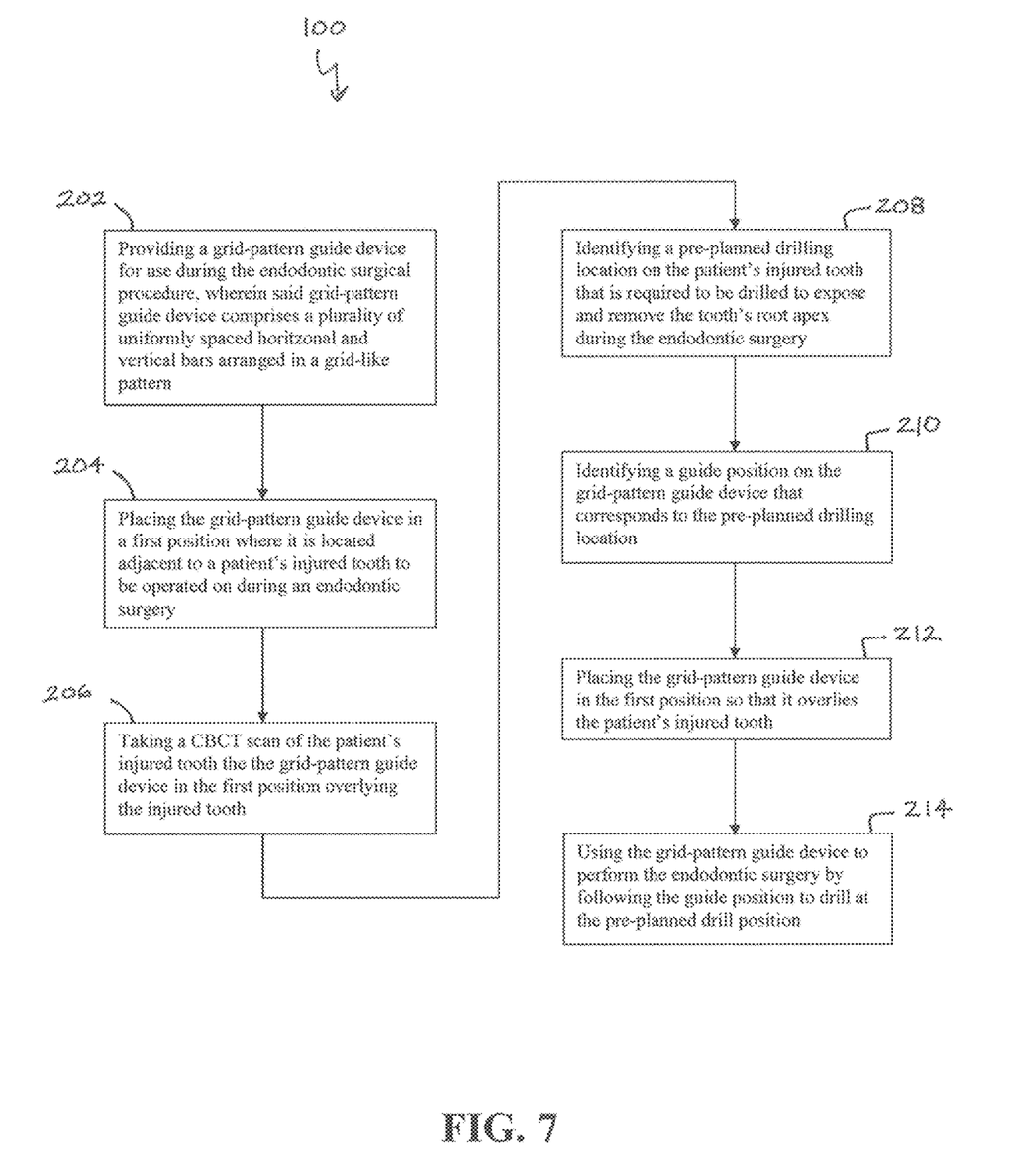
FIG. 7 is a flow chart for a method for using a grid-pattern guide device to perform an endodontic surgical procedure in accordance with another embodiment of the present invention.

Turning now to FIGS. 6 and 7, method 100 for performing an endodontic surgical procedure with the assistance of a grid-pattern guide device will be described in greater detail in accordance with select embodiments of the present invention. As described above, method 100 can be utilized during the performance of an endodontic surgical procedure where the root apex of an injured tooth must be exposed and removed, which can be accurately accomplished by utilizing a grid-pattern guide device, such as device 10 of the present invention. As shown in FIG. 6, according to one embodiment, method 100 can comprise steps 102-108. At step 102, a grid-pattern guide device can be positioned adjacent to a patient's tooth and a CBCT scan can be taken of the grid-pattern guide device and the patient's tooth. At step 104, a guide position on the grid-pattern guide device can be identified by determining a pre-planned drilling location for the patient's tooth on the CBCT scan and selecting the location on the grid-pattern guide device that aligns with an corresponds to the pre-planned drilling location. Then at step 106, the guide position can be used during the endodontic surgical procedure to assist a dental professional in properly drilling at the pre-planned drilling location and exposing the root apex of the patient's tooth.

FIG. 7 illustrates a second embodiment of method 100 with additional detailed steps of performing the endodontic surgical procedure with the assistance of the grid-pattern guide device. As shown in FIG. 7, method 100 can begin at step 202 by providing a grid-pattern guide device comprising a plurality of uniformly or non-uniformly spaced bars arranged in one or more directions to provide a grid-like pattern. Depending on the particular configuration of the guide device, cross bars can be arranged in a singular direction (e.g., only vertically), can be arranged in a traditional cross-grid pattern (e.g., in both the horizontal and vertical directions), or any other suitable arrangement. Such a device can be configured as device 10 described above in accordance with one embodiment of method 100. At step 204, the grid-pattern guide device can be placed to the side of an injured tooth to be operated upon in a first position. At step 206, a CBCT scan can be captured of the grid-pattern guide device in the first position while it overlies the injured tooth. During steps 204 and 206, according to one embodiment the grid-pattern guide device can be connected to a bitewing holder having impression material so that the first position of the grid-pattern guide device relative to the injured tooth can be subsequently re-created during surgery.

Next, at step 208, a pre-planned drilling location for the patient's injured tooth can be identified on the CBCT scan image, and then subsequently, at step 210, a corresponding guide position can be identified on the grid-pattern guide device. The pre-planned drilling location can be the location on the patient's injured tooth that needs to be removed to expose and remove the root apex of the injured tooth during the endodontic surgery. The corresponding guide position can be the location on the grid-pattern guide device that aligns with the pre-planned drilling location for the patient's injured tooth. During step 210, the guide position can be first identified on the CBCT image by matching it to the pre-planned drilling location, and then subsequently in the physical grid-pattern guide device by matching the cross bars on the actual grid-pattern guide device to those depicted in the CBCT scan. According to one embodiment, the guide position is determined relative to the uniformly spaced horizontal and vertical bars forming the grid-pattern of the grid-pattern guide device. According to one embodiment, the guide position is determined as coordinates corresponding to the uniformly spaced horizontal and vertical bars forming the grid-pattern of the grid-pattern guide device.

Next, at step 212, the grid-pattern guide device is placed into the first position so that it overlies the patient's injured tooth in the same location during the CBCT scan of step 206. Once the grid-pattern guide device is provided in the first position, at step 214, the guide position can be used to drill the patient's injured tooth along the pre-planned drill path and the endodontic surgery can be completed. As described above with reference to device 10, the guide position on the grid-pattern guide device can be used by a dental professional to locate the pre-planned drilling position that was identified on the CBCT scan during the actual endodontic surgical procedure.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art.

The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A device comprising:
   a perimeter rim defining an opening therein; and
   a plurality of cross bars arranged in a grid pattern across said opening;
   wherein said device is capable of use with a cone beam computed tomography (CBCT) scan;
   wherein said perimeter rim and said plurality of cross bars are constructed from a radiopaque material visible on the CBCT scan;
   wherein said device is attachable to a bitewing holder having a film portion and a lateral bite tab to maintain said device in a fixed position relative to a patient's tooth during the CBCT scan and during performance of an apicoectomy procedure, wherein said devices is attachable by a first side of the device being securable by an impression material to an exterior side of the film portion of the bitewing holder so that the device extends at least a portion below the lateral bite tab and is configured for placement in a position adjacent a buccal side of a person's tooth between the tooth and an interior side of the person's cheek, said attachment enabling the device to be removable after taking the CBCT scan and returned to the position during the apicoectomy procedure after removal of tissue adjacent the tooth to permit access to the tooth through at least one of the plurality of cross bars.

2. The device of claim 1, wherein said plurality of cross bars comprises a plurality of longitudinal cross bars extending between side edges of said perimeter rim and a plurality of latitudinal cross bars extending between top and bottom edges of said perimeter rim.

3. The device of claim 2, wherein said plurality of longitudinal cross bars are parallel to one another and uniformly spaced apart and wherein said plurality of latitudinal cross bars are parallel to one another and uniformly spaced apart.

4. The device of claim 3, wherein said plurality of longitudinal cross bars are perpendicular to said plurality of latitudinal cross bars.

5. The device of claim 4, further comprising the bitewing holder, wherein said device is configured as an integrated bitewing holder with said perimeter rim and said plurality of cross bars.

6. The device of claim 1, wherein at least one of said plurality of longitudinal cross bars and said plurality of latitudinal cross bars have a non-uniform spacing.

7. The device of claim 1, wherein said perimeter rim has a rectangular shape.

8. The device of claim 1, wherein said perimeter rim and said plurality of cross bars are constructed from at least one of titanium alloy, tungsten and stainless steel.

9. The device of claim 1, further comprising a locator dot secured to said plurality of cross bars within said opening, wherein said locator dot is configured for enabling the identification of a particular location within said opening.

10. The device of claim 9, wherein said locator dot is centrally located within said opening.

11. A method for locating a root apex of an identified tooth embedded in bone, said method comprising the steps of:
providing a grid-pattern guide device adjacent to said identified tooth and capturing a cone beam computed tomography scan image of said grid-pattern guide device and said identified tooth, wherein said grid-pattern guide device comprises a grid structure having a plurality of intermediate cross bars, the grid-pattern guide device being attachable by an impression material to a bitewing holder having a film portion and a lateral bite tab, said bitewing holder being attachable by a first side of the grid-pattern guide device being securable by a registration material to an exterior side of the film portion of the bitewing holder so that the grid-pattern guide device extends at least a portion below the lateral bite tab and is configured for placement in a position adjacent a buccal side of said identified tooth between the tooth and a portion of an interior side of an adjacent cheek, said attachment enabling the device to be removed after taking the CBCT scan and returned to the position after removal of tissue adjacent the tooth during an apicoectomy procedure to permit access to the tooth through at least one of the plurality of intermediate cross bars;
identifying a guide position on said grid-pattern guide device by determining a pre-planned drilling location on said cone beam computed tomography scan image corresponding to a position on said identified tooth where said root apex is located and selecting a location on said grid-pattern guide device that corresponds to said pre-planned drilling location; and
locating said guide position and identifying a drill location associated with the guide position, wherein said drill location corresponds to the root apex location of said identified tooth.

12. The method of claim 11, wherein said grid structure of said grid-pattern guide device comprises a plurality of longitudinal cross bars and a plurality of latitudinal cross bars.

13. The method of claim 11, wherein said grid structure of said grid-pattern guide device comprises a single set of cross bars, wherein said single set of cross bars comprises a plurality of cross bars extending in the same direction.

14. The method of claim 11, further comprising the step of securing said grid-pattern guide device to a bitewing holder.

15. The method of claim 11, further comprising the steps of:
placing said grid-pattern guide device in a first position relative to said identified tooth when taking said cone beam computed tomography scan image;
removing said grid pattern guide device from said first position and identifying said guide position on said grid pattern guide device; and
placing said grid-pattern guide device in said first position when performing an endodontic surgical procedure.

16. A method for removing a root apex of an identified tooth, said method comprising the steps of:
providing a grid-pattern guide device comprising at least one of a plurality of spaced horizontal bars and a plurality of spaced vertical bars arranged in a grid structure, the grid-pattern guide device being attached to a bitewing holder having a film portion and a lateral bite tab, said bitewing holder being attachable by a first side of the grid-pattern guide device being secured by an impression material to an exterior side of the film portion of the bitewing holder so that the grid-pattern guide device extends at least a portion below the lateral bite tab and is configured for placement in a position adjacent a buccal side of said identified tooth between the tooth and a portion of an interior side of a cheek adjacent the tooth, wherein, when said bitewing holder is attached to the grit-pattern guide device, said grit-pattern guide device is enabled to be removed after taking the CBCT scan and returned to the position after removal of tissue adjacent the tooth during an apicoectomy procedure to permit access to the tooth through at least one of the plurality of intermediate cross bars;
placing said grid-pattern guide device in a first position where said grid-pattern guide device is located adjacent to the identified tooth;
taking a cone beam computed tomography scan image of said grid-pattern guide device in said first position overlying said identified tooth;
removing said grid pattern guide device from said first position;
identifying a pre-planned drilling location on said identified tooth associated with said root apex;

identifying a guide position on said grid-pattern guide device that corresponds to said pre-planned drilling location;

placing said grid-pattern guide device in said first position overlying said identified tooth; and removing the root apex of the identified tooth by using said grid-pattern guide device to locate said root apex, and drilling at said pre-planned drill position.

17. The method of claim 16, wherein said grid-pattern guide device is secured to a bitewing holder.

18. The method of claim 17, further comprising the step of applying an impression material to said bitewing holder.

\* \* \* \* \*